US 8,551,179 B2

(12) United States Patent
Jones et al.

(10) Patent No.: US 8,551,179 B2
(45) Date of Patent: Oct. 8, 2013

(54) FEMORAL PROSTHESIS SYSTEM HAVING PROVISIONAL COMPONENT WITH VISUAL INDICATORS

(75) Inventors: Nolan C. Jones, Warsaw, IN (US); Jeffery A. VanDiepenbos, Syracuse, IN (US); Abraham P. Habegger, Warsaw, IN (US); Brian D. Earl, South Bend, IN (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 13/161,624

(22) Filed: Jun. 16, 2011

(65) Prior Publication Data

US 2012/0323334 A1    Dec. 20, 2012

(51) Int. Cl.
*A61F 2/38* (2006.01)

(52) U.S. Cl.
USPC ................................ 623/20.35; 623/20.31

(58) Field of Classification Search
USPC ................... 623/20.14, 20.15, 20.31, 20.35
See application file for complete search history.

(56) References Cited

U.S. PATENT DOCUMENTS

| | | | |
|---|---|---|---|
| 4,081,866 A | 4/1978 | Upshaw et al. | |
| 4,340,978 A | 7/1982 | Buechel et al. | |
| 4,944,756 A | 7/1990 | Kenna | |
| 4,950,298 A | 8/1990 | Gustilo et al. | |
| 4,959,071 A | 9/1990 | Brown et al. | |
| 5,007,933 A | 4/1991 | Sidebotham et al. | |
| 5,061,271 A | 10/1991 | Van Zile | |
| 5,133,758 A | 7/1992 | Hollister | |
| 5,226,915 A | 7/1993 | Bertin | |
| 5,282,861 A | 2/1994 | Kaplan | |
| 5,282,869 A | 2/1994 | Miyajima et al. | |
| 5,326,361 A | 7/1994 | Hollister | |
| 5,549,686 A | 8/1996 | Johnson et al. | |
| 5,609,643 A | 3/1997 | Colleran et al. | |
| 5,871,546 A | 2/1999 | Colleran et al. | |
| 5,879,393 A | 3/1999 | Whiteside et al. | |
| 5,935,173 A | 8/1999 | Roger et al. | |

(Continued)

FOREIGN PATENT DOCUMENTS

| | | |
|---|---|---|
| DE | 202007014128 U1 | 1/2008 |
| EP | 0303467 A2 | 2/1989 |

(Continued)

OTHER PUBLICATIONS

Partial Search Report mailed Jul. 3, 2012 in International Application No. PCT/US2012/038531 from the International Searching Authority.

(Continued)

*Primary Examiner* — David Isabella
*Assistant Examiner* — Randy Shay
(74) *Attorney, Agent, or Firm* — Schwegman Lundberg & Woessner, P.A.

(57) ABSTRACT

A provisional femoral component, in one embodiment, including at least one first visual indicator and at least one second visual indicator, the first and second visual indicators providing indicating means for simultaneously visually representing a first profile of a first femoral prosthesis and a second profile of a second femoral prosthesis. In another embodiment, a provisional femoral component including a patellofemoral flange having two sulci and a central ridge between the two sulci. In this manner, the provisional femoral component can be positioned on a resected distal femur surface of both a right and left knee joint.

5 Claims, 8 Drawing Sheets

(56) References Cited

U.S. PATENT DOCUMENTS

| | | | |
|---|---|---|---|
| 6,039,764 A | 3/2000 | Pottenger et al. | |
| 6,074,424 A | 6/2000 | Perrone, Jr. et al. | |
| 6,152,960 A | 11/2000 | Pappas | |
| 6,197,064 B1 | 3/2001 | Haines et al. | |
| 6,264,697 B1 | 7/2001 | Walker | |
| 6,364,911 B1 | 4/2002 | Schmotzer et al. | |
| 6,540,787 B2 | 4/2003 | Biegun et al. | |
| 6,589,283 B1 | 7/2003 | Metzger et al. | |
| 6,699,291 B1 | 3/2004 | Augoyard et al. | |
| 6,893,467 B1 | 5/2005 | Bercovy | |
| 7,081,137 B1 | 7/2006 | Servidio | |
| 7,297,164 B2 | 11/2007 | Johnson et al. | |
| 7,306,609 B2 | 12/2007 | Schmotzer et al. | |
| 7,413,577 B1 | 8/2008 | Servidio | |
| 7,465,320 B1 | 12/2008 | Kito et al. | |
| 7,678,152 B2 | 3/2010 | Suguro et al. | |
| 8,062,377 B2 | 11/2011 | Haines | |
| 8,088,167 B2 | 1/2012 | Haines | |
| 2003/0158606 A1 | 8/2003 | Coon et al. | |
| 2003/0225458 A1 | 12/2003 | Donkers et al. | |
| 2004/0039450 A1* | 2/2004 | Griner et al. | 623/20.31 |
| 2004/0243245 A1 | 12/2004 | Plumet et al. | |
| 2005/0055102 A1 | 3/2005 | Tornier et al. | |
| 2005/0143832 A1 | 6/2005 | Carson | |
| 2005/0177169 A1 | 8/2005 | Fisher et al. | |
| 2005/0283249 A1 | 12/2005 | Carson | |
| 2006/0265078 A1 | 11/2006 | Mcminn | |
| 2006/0265080 A1 | 11/2006 | Mcminn | |
| 2007/0135925 A1 | 6/2007 | Walker | |
| 2007/0135926 A1 | 6/2007 | Walker | |
| 2007/0150066 A1 | 6/2007 | McMinn et al. | |
| 2007/0260323 A1 | 11/2007 | Earl et al. | |
| 2008/0058947 A1 | 3/2008 | Earl et al. | |
| 2008/0058948 A1 | 3/2008 | Biegun et al. | |
| 2008/0097615 A1 | 4/2008 | Lipman et al. | |
| 2008/0114463 A1 | 5/2008 | Auger et al. | |
| 2008/0119940 A1 | 5/2008 | Otto et al. | |
| 2008/0140212 A1 | 6/2008 | Metzger et al. | |
| 2008/0243258 A1 | 10/2008 | Sancheti | |
| 2008/0288080 A1 | 11/2008 | Sancheti | |
| 2009/0036992 A1 | 2/2009 | Tsakonas | |
| 2009/0043395 A1 | 2/2009 | Hotokebuchi et al. | |
| 2009/0062924 A1 | 3/2009 | Kito et al. | |
| 2009/0265011 A1 | 10/2009 | Mandell | |
| 2009/0265013 A1 | 10/2009 | Mandell | |
| 2009/0306787 A1 | 12/2009 | Crabtree et al. | |
| 2009/0319047 A1 | 12/2009 | Walker | |
| 2009/0319048 A1 | 12/2009 | Shah et al. | |
| 2009/0319049 A1 | 12/2009 | Shah et al. | |
| 2009/0326663 A1 | 12/2009 | Dun | |
| 2009/0326665 A1 | 12/2009 | Wyss et al. | |
| 2009/0326666 A1 | 12/2009 | Wyss et al. | |
| 2009/0326667 A1 | 12/2009 | Williams et al. | |
| 2010/0036499 A1 | 2/2010 | Pinskerova | |
| 2010/0036500 A1 | 2/2010 | Heldreth et al. | |
| 2010/0042224 A1 | 2/2010 | Otto et al. | |
| 2010/0161067 A1 | 6/2010 | Saleh et al. | |
| 2011/0022179 A1 | 1/2011 | Andriacchi et al. | |
| 2011/0093083 A1 | 4/2011 | Earl et al. | |
| 2011/0218541 A1 | 9/2011 | Bailey et al. | |
| 2011/0307067 A1* | 12/2011 | Dees | 623/20.35 |
| 2012/0323335 A1 | 12/2012 | Parisi et al. | |
| 2012/0323336 A1 | 12/2012 | Parisi et al. | |
| 2012/0323337 A1 | 12/2012 | Parisi et al. | |
| 2013/0006370 A1* | 1/2013 | Wogoman et al. | 623/20.16 |
| 2013/0006371 A1* | 1/2013 | Wogoman et al. | 623/20.21 |
| 2013/0006376 A1* | 1/2013 | Wogoman et al. | 623/20.32 |
| 2013/0006378 A1* | 1/2013 | Wogoman | 623/20.35 |

FOREIGN PATENT DOCUMENTS

| | | |
|---|---|---|
| EP | 0376658 B1 | 6/1994 |
| EP | 0381352 B1 | 6/1994 |
| EP | 0567705 B1 | 7/1997 |
| EP | 0993812 A2 | 4/2000 |
| EP | 1013232 A2 | 6/2000 |
| EP | 1285638 A2 | 2/2003 |
| EP | 1033117 B1 | 6/2004 |
| EP | 0975286 B1 | 8/2004 |
| EP | 1477142 A2 | 11/2004 |
| EP | 1477143 A1 | 11/2004 |
| EP | 1285638 B1 | 11/2005 |
| EP | 1719478 A2 | 11/2006 |
| EP | 1722721 A1 | 11/2006 |
| EP | 1354571 B1 | 6/2007 |
| EP | 1862150 A1 | 12/2007 |
| EP | 2004099 A2 | 12/2008 |
| EP | 1867302 B1 | 9/2009 |
| EP | 2147660 A1 | 1/2010 |
| EP | 2158878 A1 | 3/2010 |
| JP | 2004166802 A | 6/2004 |
| WO | WO-9535074 A1 | 12/1995 |
| WO | WO-0023010 A1 | 4/2000 |
| WO | WO-2004016204 A1 | 2/2004 |
| WO | WO-2005037147 A1 | 4/2005 |
| WO | WO-2005122967 A1 | 12/2005 |
| WO | WO2008/054389 A1 | 5/2008 |
| WO | WO-2009088234 A2 | 7/2009 |
| WO | WO-2009088236 A2 | 7/2009 |
| WO | WO-2009088238 A2 | 7/2009 |
| WO | WO-2009105495 A1 | 8/2009 |
| WO | WO-2010108550 A1 | 9/2010 |
| WO | WO-2012173704 A1 | 12/2012 |
| WO | WO-2012173706 A1 | 12/2012 |
| WO | WO-2012173740 A1 | 12/2012 |

OTHER PUBLICATIONS

Zimmer Gender Solutions Patello-Femoral Joint (PFJ) System, Surgical Technique, 39 pages, Zimmer, Inc. 2008, 2009.

Zimmer Unicompartmental High Flex Knee, Intramedullary, Spacer Block Option and Extramedullary Minimally Invasive Surgical Techniques, 62 pages, Zimmer, Inc. 2004, 2009, 2010.

"U.S. Appl. No. 13/459,060, Preliminary Amendment filed Apr. 27, 2012", 6 pgs.

"U.S. Appl. No. 13/459,061, Preliminary Amendment filed Apr. 27, 2012", 6 pgs.

"U.S. Appl. No. 13/459,064, Preliminary Amendment filed Apr. 27, 2012", 6 pgs.

"Gender Solutions Natural-Knee Flex System", Zimmer, Inc., (2007, 2009), 6 pgs.

"Gender Solutions Natural-Knee Flex System: Surgical Technique", Zimmer, Inc., (2007, 2008, 2009), 36 pgs.

"International Application Serial No. PCT/US2012/035688, Search Report mailed Sep. 17, 2012", 7 pgs.

"International Application Serial No. PCT/US2012/035688, Written Opinion mailed Sep. 17, 2012", 11 pgs.

"International Application Serial No. PCT/US2012/035691, Partial Search Report mailed Jul. 10, 2012", 8 pgs.

"International Application Serial No. PCT/US2012/035691, Search Report mailed Sep. 17, 2012", 7 pgs.

"International Application Serial No. PCT/US2012/035691, Written Opinion mailed Sep. 17, 2012", 11 pgs.

"International Application Serial No. PCT/US2012/035693, Partial Search Report mailed Jun. 27, 2012", 8 pgs.

"International Application Serial No. PCT/US2012/035693, Search Report mailed Oct. 9, 2012", 7 pgs.

"International Application Serial No. PCT/US2012/035693, Written Opinion mailed Oct. 9, 2012", 11 pgs.

"International Application Serial No. PCT/US2012/038531, Search Report mailed Oct. 8, 2012", 14 pgs.

"International Application Serial No. PCT/US2012/038531, Written Opinion mailed Oct. 8, 2012", 10 pgs.

"LPS-Flex Fixed Bearing Knee: Surgical Technique", Zimmer, Inc., (2004, 2007, 2008), 16 pgs.

"NexGen Complete Knee Solution Extramedullary/Intramedullary Tibial Resector: Surgical Technique", Zimmer, Inc., (2000, 2008, 2009), 28 pgs.

(56) References Cited

OTHER PUBLICATIONS

"NexGen Complete Knee Solution: Surgical Technique for the CR-Flex Fixed Bearing Knee", Zimmer, Inc., (2003), 22 pgs.

"NexGen Implant Options Surgeon-Specific", Zimmer Inc., 16 pgs.

"NexGen LPS Fixed Knee: Surgical Technique", Zimmer Inc., (2002, 2008), 44 pgs.

"NexGen LPS-Flex Mobile and LPS-Mobile Bearing Knees", Zimmer, Inc., (2007, 2008), 4 pgs.

* cited by examiner

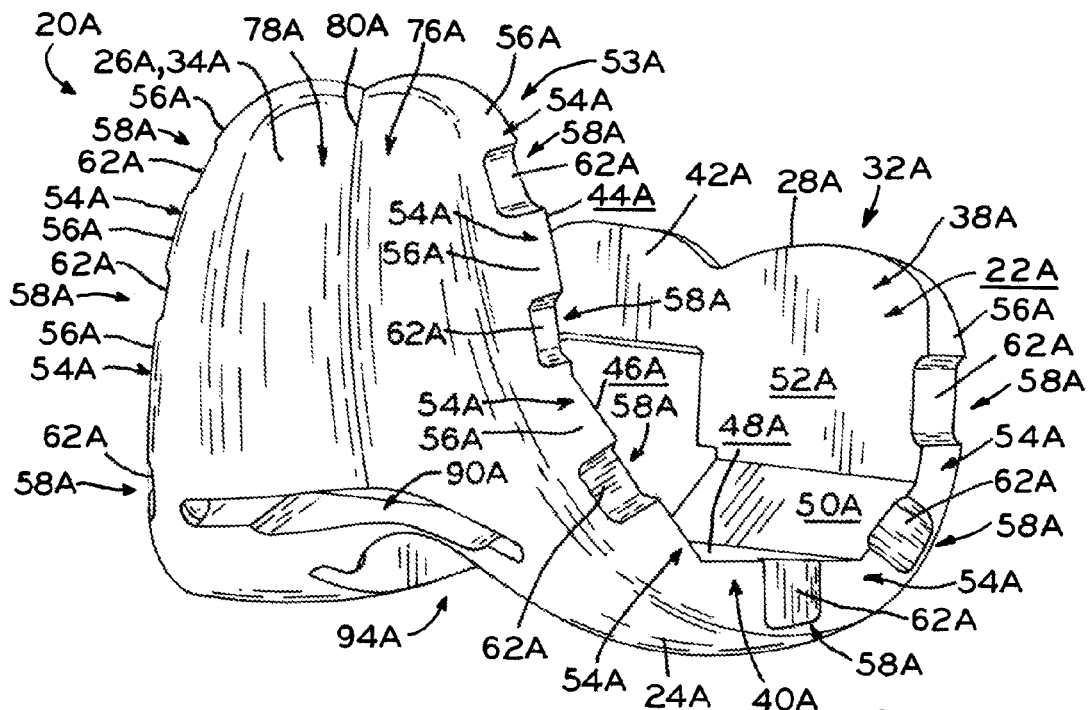
FIG_1
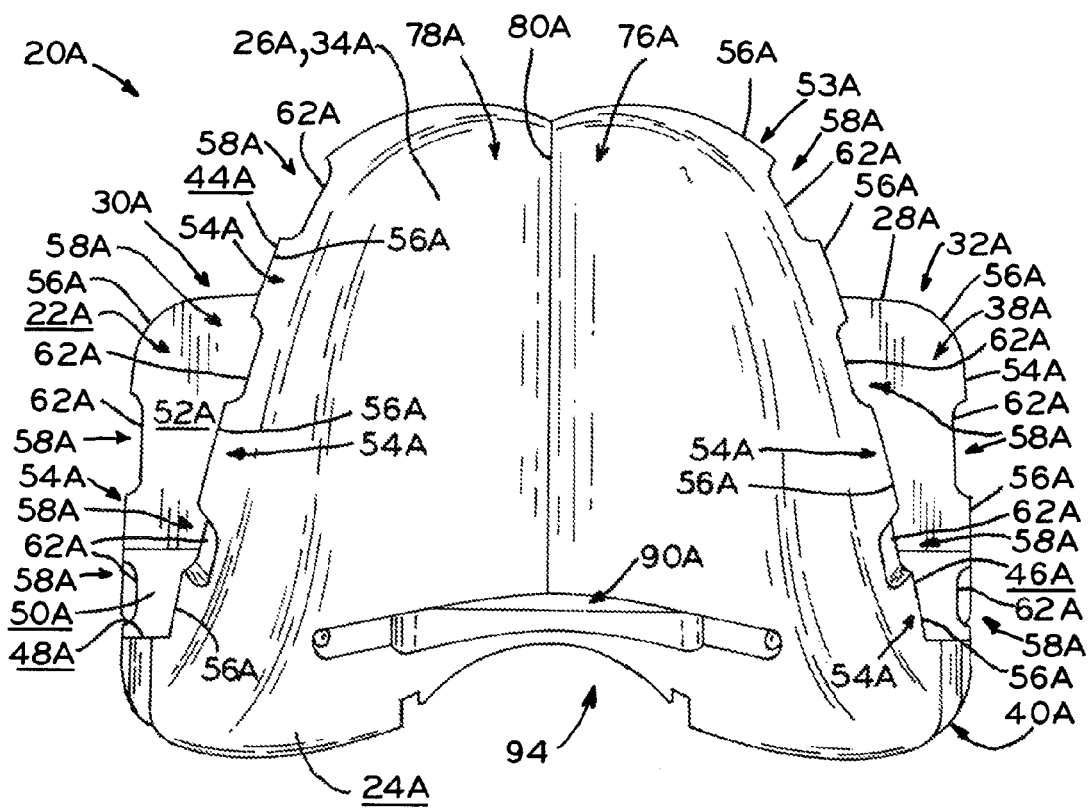
FIG_2

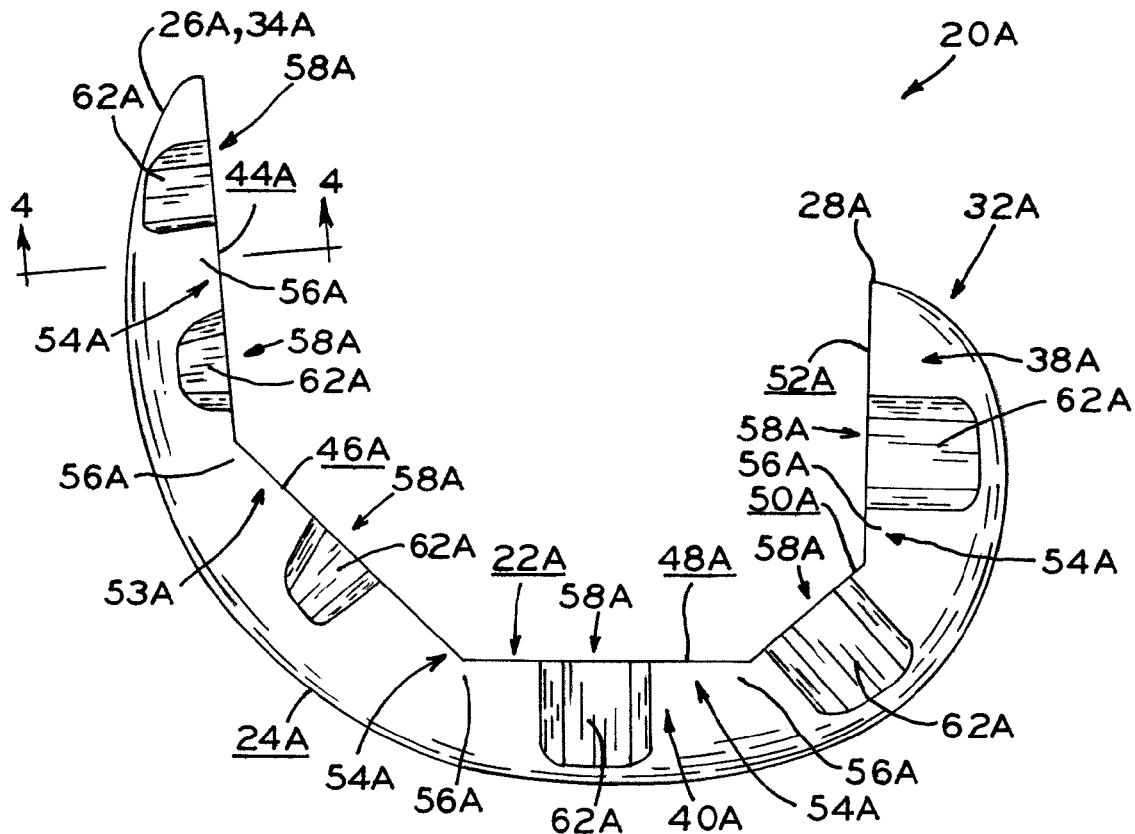
FIG_3
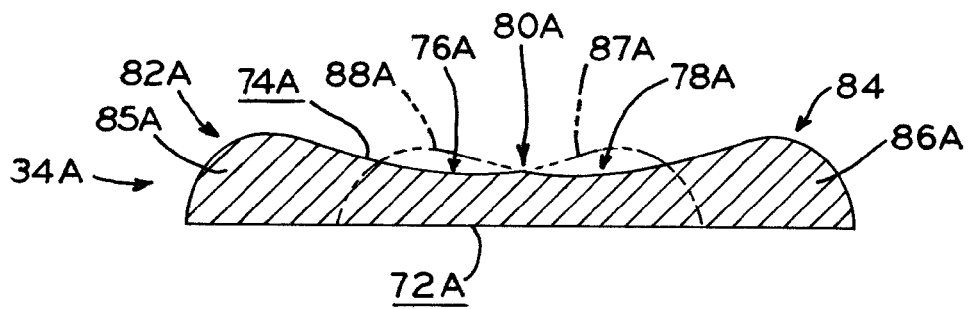
FIG_4

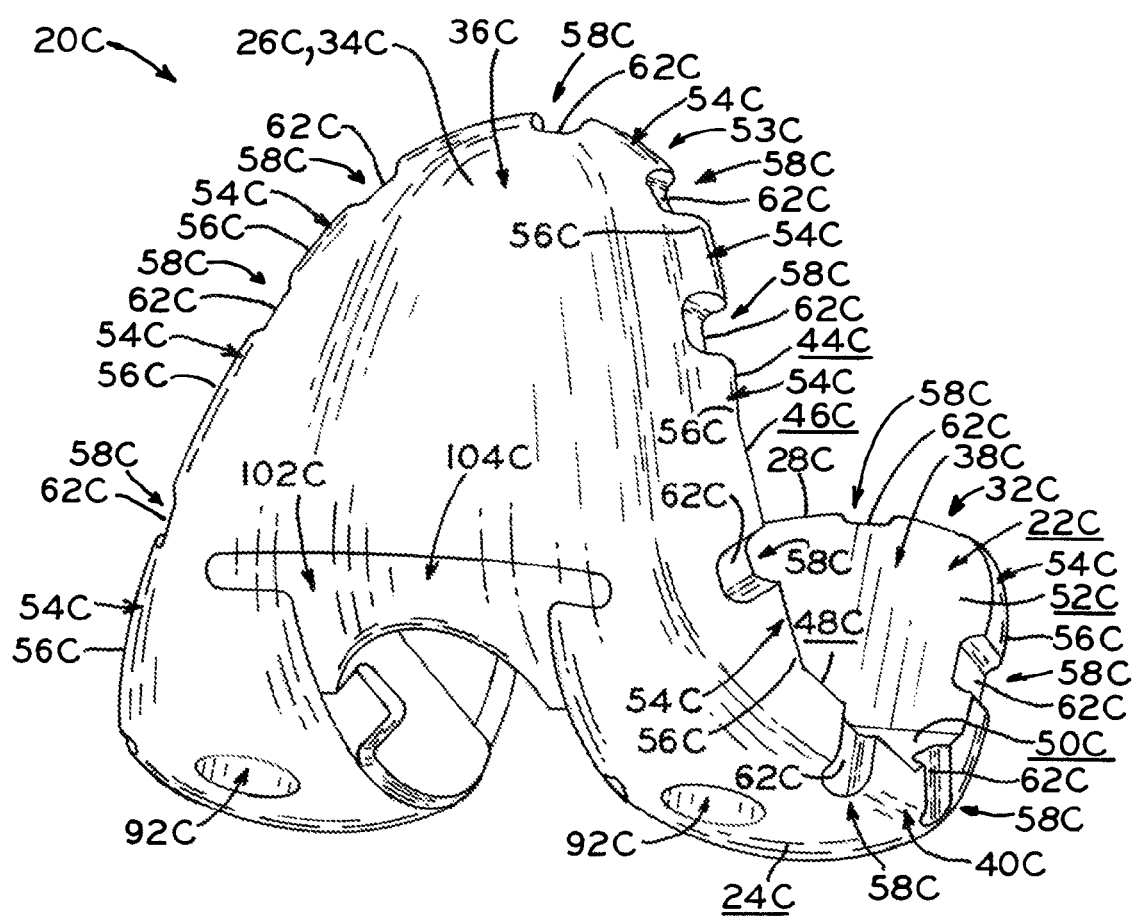
FIG_12

# FEMORAL PROSTHESIS SYSTEM HAVING PROVISIONAL COMPONENT WITH VISUAL INDICATORS

BACKGROUND

1. Field of the Disclosure

The present disclosure relates generally to provisional orthopedic components used to replicate final orthopedic components during a surgical procedure. More particularly, the present disclosure relates to provisional femoral components that assist in determining the proper size of final prosthetic components for replacement of all or part of a natural knee joint.

2. Description of the Related Art

Knee replacement provisional components are positioned on a distal femur and/or a proximal tibia to allow range of motion testing so that a surgeon can verify joint kinematics and/or proper sizing of final prosthetic components. In certain surgical procedures, a surgeon may remove and replace a provisional femoral component of a first size with a provisional femoral component of a second size to adjust the ligament tension of the knee joint and/or to evaluate the M/L (medial/lateral) sizing of the provisional femoral component. For example, a first provisional femoral component having a first size can correspond to a standard sized femoral prosthesis and a second provisional femoral component having a second size can correspond to a narrow sized femoral prosthesis. Such systems require a provisional femoral component for each different sized femoral prosthesis. During knee surgery, a surgeon may selectively remove and replace a provisional femoral component of a first size with a provisional femoral component of a second size to adjust the ligament tension of the knee joint and/or to evaluate the M/L sizing of the provisional femoral component and determine which femoral prosthesis should be selected for final implantation in a knee joint.

SUMMARY

The present disclosure provides a provisional femoral component which, in one embodiment, includes at least one first visual indicator and at least one second visual indicator, the first and second visual indicators providing indicating means for simultaneously visually representing a first profile of a first femoral prosthesis and a second profile of a second femoral prosthesis. In the system of the present disclosure, only one provisional femoral component is needed which can simultaneously visually represent two different femoral prosthesis profiles, as opposed to a system that requires a provisional femoral component for each different sized femoral prosthesis. In another embodiment, the present disclosure provides a provisional femoral component including a patellofemoral flange having two sulci and a central ridge between the two sulci. In this manner, the provisional femoral component can be positioned on a resected distal femur surface of both a right and left knee joint. In the system of the present disclosure, only one provisional femoral component is needed which can be positioned on a resected distal femur surface of both a right and left knee joint, as opposed to a system that requires a left provisional femoral component for a left knee and a separate right provisional femoral component for a right knee.

The present disclosure, in one form thereof, comprises a femoral prosthesis system including a first femoral prosthesis including a first condyle defining a first articulating surface and an opposing first bone contacting surface, and a first peripheral wall spanning the first articulating surface and the first bone contacting surface, the first peripheral wall defining a first profile. The femoral prosthesis system further includes a second femoral prosthesis including a second condyle defining a second articulating surface and an opposing second bone contacting surface, and a second peripheral wall spanning the second articulating surface and the second bone contacting surface, the second peripheral wall defining a second profile, wherein the second profile is different than the first profile. The femoral prosthesis system further includes a provisional femoral component including a provisional condyle defining a provisional articulating surface and an opposing provisional bone contacting surface, a provisional peripheral wall spanning the provisional articulating surface and the provisional bone contacting surface, and at least one visual indicator and at least one second visual indicator spaced along the provisional peripheral wall, the at least one first visual indicator visually representing the first profile of the first femoral prosthesis, and the at least one second visual indicator visually representing the second profile of the second femoral prosthesis.

The present disclosure, in another form thereof, comprises a provisional femoral component including a provisional condyle defining a provisional articulating surface sized and shaped to be engageable with a proximal tibia in joint articulating relationship and an opposing provisional bone contacting surface sized and shaped to be engageable with a distal femur, and indicating means for simultaneously visually representing two different femoral prosthesis profiles.

The present disclosure, in a further form thereof, comprises a method of determining a size of a femoral prosthesis for a prosthetic knee joint, the knee joint including a proximal tibia and a distal femur, the method comprising: obtaining a femoral prosthesis system including a first femoral prosthesis including a first condyle defining a first articulating surface and an opposing first bone contacting surface, and a first peripheral wall spanning the first articulating surface and the first bone contacting surface, the first peripheral wall defining a first profile; a second femoral prosthesis including a second condyle defining a second articulating surface and an opposing second bone contacting surface, and a second peripheral wall spanning the second articulating surface and the second bone contacting surface, the second peripheral wall defining a second profile, wherein the second profile is different than the first profile; and a provisional femoral component including a provisional condyle defining a provisional articulating surface and an opposing provisional bone contacting surface, a provisional peripheral wall spanning the provisional articulating surface and the provisional bone contacting surface, and at least one first visual indicator and at least one second visual indicator spaced along the provisional peripheral wall, the at least one first visual indicator visually representing the first profile of first femoral prosthesis, and the at least one second visual indicator visually representing the second profile of the second femoral prosthesis; positioning the provisional bone contacting surface of the provisional component on a resected distal femur surface; and selecting one of the first femoral prosthesis and the second femoral prosthesis for implantation in the knee joint based on one of the at least one first visual indicator and the at least one second visual indicator.

The present disclosure, in another form thereof, comprises a provisional femoral component including a patellofemoral flange including a bone contacting, non-articulating surface and an articulating surface opposite the bone contacting surface, the articulating surface including a first sulcus formed in the patellofemoral flange, a second sulcus formed in the patellofemoral flange, a central ridge disposed between the first sulcus and the second sulcus, the central ridge having a first thickness, and a first anterior flange and a second anterior flange extending along respective medial/lateral peripheries of the patellofemoral flange, the first and second anterior flanges each having a second thickness greater than the first thickness of the central ridge, the central ridge, the first sulcus, and the second sulcus each disposed between the first and second anterior flanges.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein:

FIG. 1 is a perspective view of a provisional femoral component in accordance with an exemplary first embodiment of the present disclosure;

FIG. 2 is a front elevation view of the provisional femoral component of FIG. 1;

FIG. 3 is a side elevation view of the provisional femoral component of FIG. 1;

FIG. 4 is a cross-sectional view taken along line 4-4 of FIG. 3;

FIG. 12 is an assembled view showing the modular insert component of FIG. 11 attached to the provisional femoral component of FIG. 11.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 7:
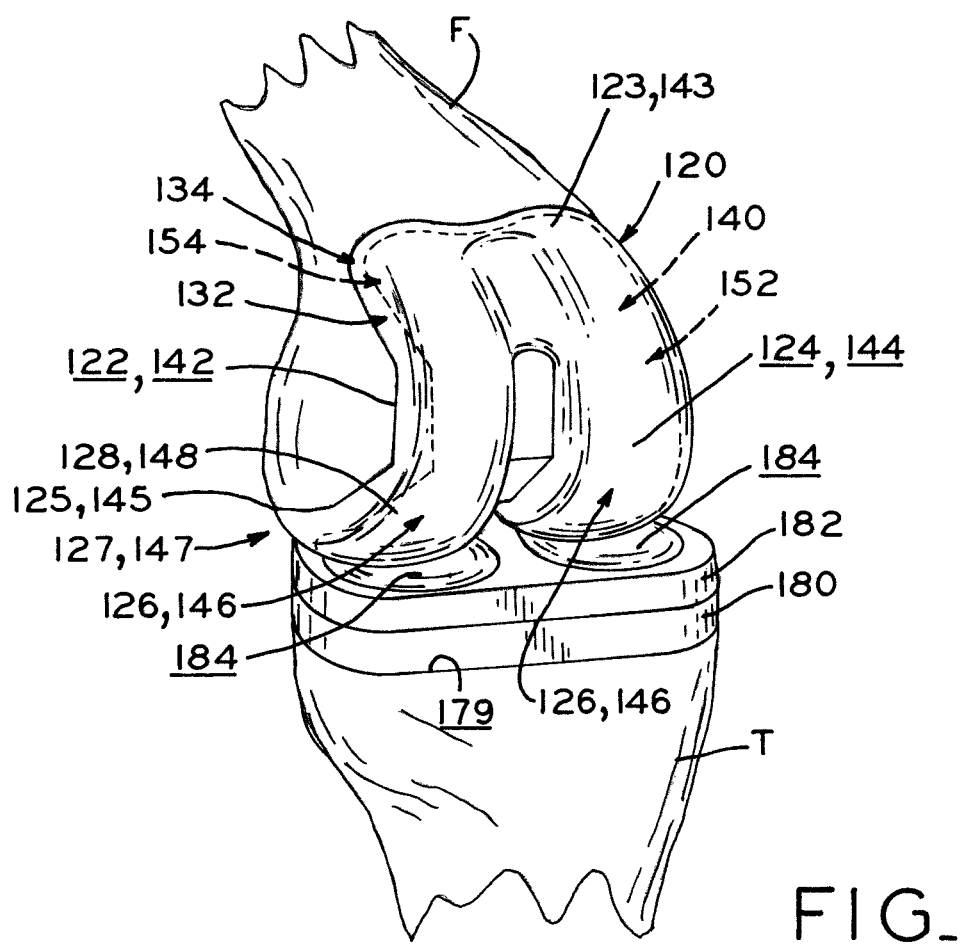
FIG. 7 is a perspective view of a knee joint illustrating a resected distal femur surface with a first femoral prosthesis having a first profile secured thereon and a resected proximal tibia surface with a tibial bearing component and a tibial base plate attached thereon, and further schematically illustrating a second femoral prosthesis having a second profile in dashed lines.

The present disclosure, in one embodiment, provides a femoral prosthesis system for determining the size of a femoral prosthesis for a prosthetic knee joint, the femoral prosthesis system including a provisional femoral component including indicating means for simultaneously visually representing two different femoral prosthesis profiles. FIG. 7 illustrates a prosthetic knee joint, the knee joint including proximal tibia T and distal femur F. In the following discussion, "proximal" refers to a direction generally toward the heart of a patient, and "distal" refers to the opposite direction of proximal, i.e., away from the heart of a patient. As used herein, "anterior" refers to a direction generally toward the front of a patient, and "posterior" refers to the opposite direction of anterior, i.e., toward the back of a patient. Further, as used herein, "medial" refers to a direction generally toward the middle of a patient, and "lateral" refers to the opposite direction of medial, i.e., toward the side of a patient.

Figure 8:
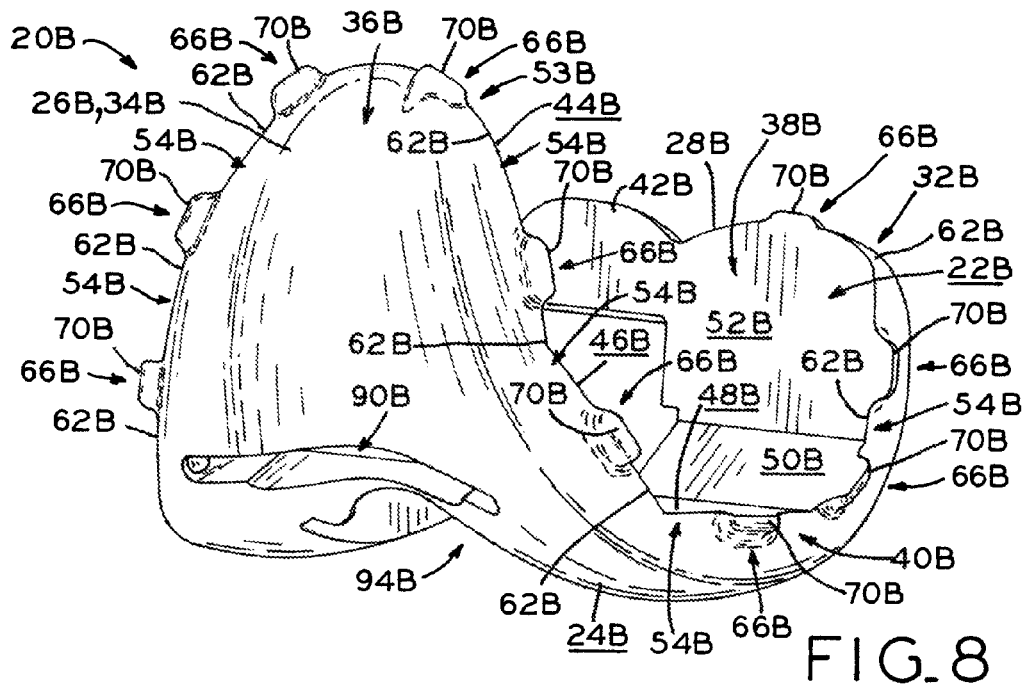
FIG. 8 is a perspective view of a provisional femoral component in accordance with an exemplary second embodiment of the present disclosure.
Figure 9:
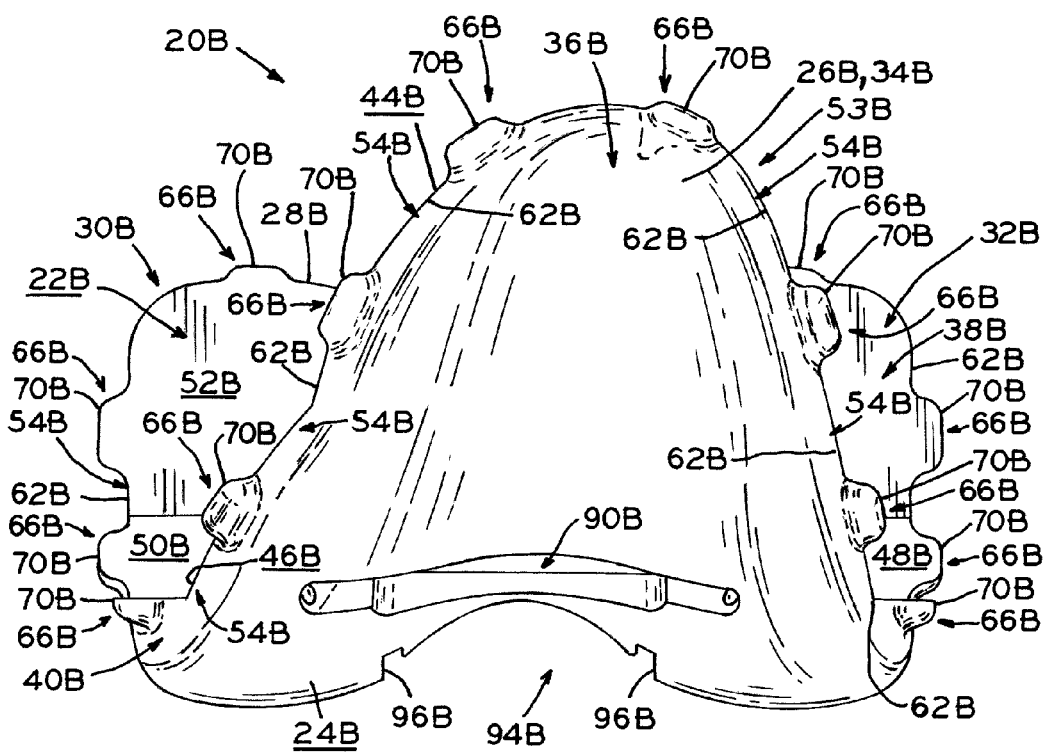
FIG. 9 is a front elevation view of the provisional femoral component of FIG. 8.
Figure 10:
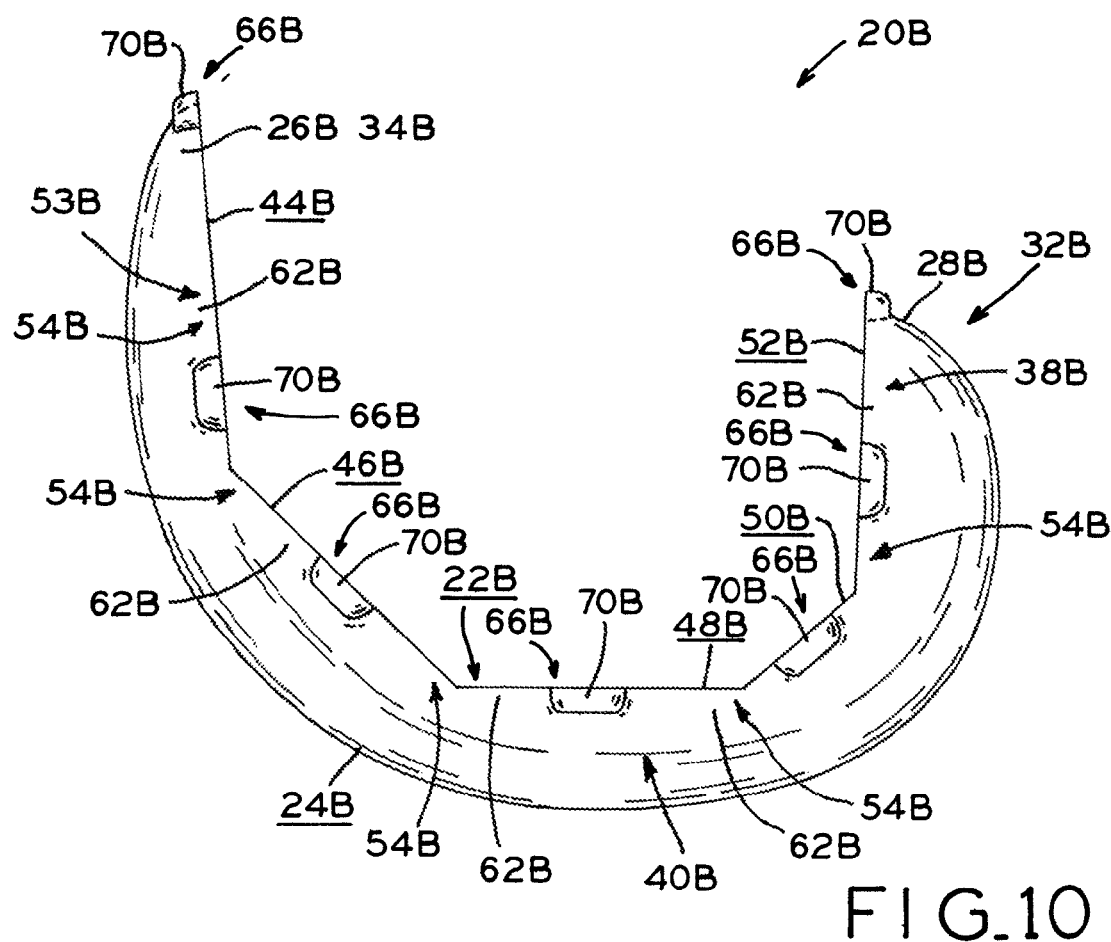
FIG. 10 is a side elevation view of the provisional femoral component of FIG. 8.
Figure 11:
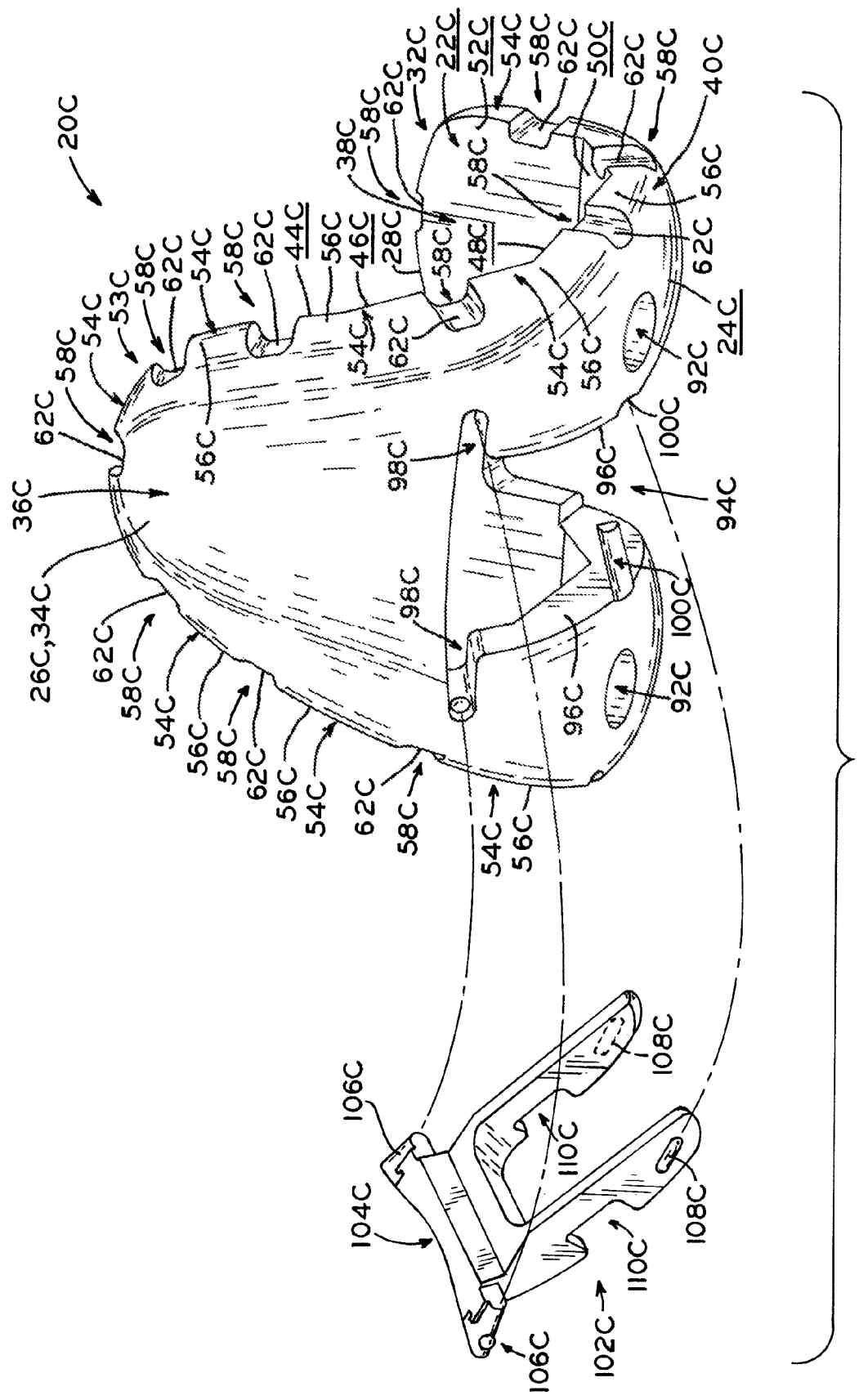
FIG. 11 is an exploded perspective view of a provisional femoral component in accordance with an exemplary third embodiment of the present disclosure and a modular insert component.

The disclosed embodiments of the present disclosure include a provisional femoral component. For example, provisional femoral component 20A is shown in FIGS. 1-6 according to an exemplary first embodiment, provisional femoral component 20B is shown in FIGS. 8-10 according to an exemplary second embodiment, and provisional femoral component 20C is shown in FIGS. 11 and 12 according to an exemplary third embodiment. In FIGS. 1-6 and 8-12, reference numbers for the provisional femoral components utilize the same numerical reference numbers with different letters to distinguish the exemplary embodiments (i.e., provisional femoral components 20A, 20B, and 20C, respectively correspond to the first, second, and third exemplary embodiments). In this manner, for the purposes of this disclosure, a reference numeral followed by A-C corresponds to a similar feature between the exemplary first through third embodiments, respectively.

The first exemplary embodiment, as illustrated in FIGS. 1-6, includes provisional femoral component 20A generally including provisional bone contacting surface 22A and opposing provisional articulating surface 24A, each extending between anterior flange 26A and posterior side 28A. Provisional bone contacting surface 22A is adapted to position and locate provisional femoral component 20A relative to a resected distal femur surface such as resected distal femur surface 160 of distal femur F shown in FIG. 5. Provisional femoral component 20A also includes first condyle 30A and second condyle 32A, with an intercondylar fossa formed between condyles 30A, 32A. Provisional articulating surface 24A is disposed generally opposite provisional bone contacting surface 22A, and is comprised of the exterior surfaces of first and second condyles 30A, 32A as well as the exterior surface of anterior flange 26A. First and second condyles 30A, 32A each include posterior condyle portion 38A and distal condyle portion 40A. Provisional femoral component 20A also includes patellofemoral flange 34A. Provisional femoral component 20A also includes femoral cam 42A formed at posterior side 28A. Femoral cam 42A spans first and second condyles 30A, 32A.

In a posterior stabilized femoral component, such as provisional femoral component 20A, cam 42A cooperates with a spine (not shown) formed in a tibial component, such as tibial bearing component 182 shown in FIG. 7, to guide or constrain motion within certain predefined boundaries. Posterior stabilized prostheses are appropriate where the posterior cruciate ligament (PCL) is torn or otherwise damaged, or where the PCL is resected during surgery.

In the exemplary embodiments of FIGS. 1-3, 5, 6 and 8-12, provisional femoral components 20A, 20B, 20C are posterior stabilized femoral components, though it is contemplated that other femoral components may be utilized in accordance with the present disclosure such as femoral components which cooperate to form a cruciate retaining prosthesis, for example. Provisional femoral components 20A, 20B, 20C may also be made available in a variety of shapes and sizes to accommodate a variety of differing knee physiologies.

Figure 5:
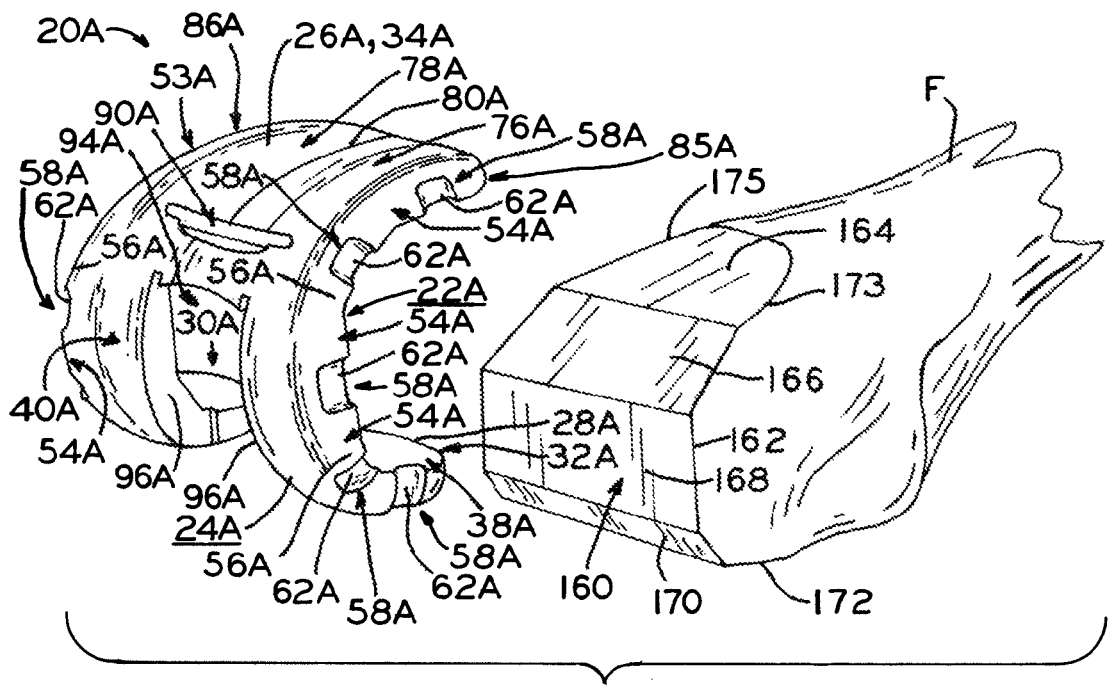
FIG. 5 is a perspective view of the provisional femoral component of FIG. 1 positioned adjacent a resected surface of a distal femur.

Referring to FIG. 3, provisional bone contacting surface 22A of provisional femoral component 20A is adapted to mate with a resected articular surface of a distal femur, such as resected distal femur surface 160 of distal femur F shown in FIG. 5, and includes anterior facet 44A, anterior chamfer facet 46A, distal facet 48A, posterior chamfer facet 50A, and posterior facet 52A. Anterior facet 44A, anterior chamfer facet 46A, distal facet 48A, posterior chamfer facet 50A, and posterior facet 52A correspond to the cuts made to a distal end of a femur, such as distal femur F shown in FIG. 5, to allow implantation of a femoral prosthesis component, i.e., anterior cut 164, anterior chamfer cut 166, distal cut 168, posterior chamfer cut 170, and posterior cut 172 made in distal femur F to form resected distal femur surface 160 as shown in FIG. 5.

FIG. 7 illustrates first femoral prosthesis 120 and second femoral prosthesis 140 according to an exemplary embodiment of the present disclosure. First femoral prosthesis 120 generally includes first bone contacting surface 122 and opposing first articulating surface 124, each extending between first anterior flange 123 and first posterior side 125. First bone contacting surface 122 is adapted to affix first femoral prosthesis 120 to a distal portion of femur F, such as with bone cement and/or porous bone-ingrowth material. First femoral prosthesis 120 also includes a pair of first condyles 126, i.e., a medial condyle and a lateral condyle, each including first posterior condyle 127 and first distal condyle 128. First articulating surface 124 is disposed generally opposite first bone contacting surface 122, and is comprised of the exterior surfaces of first condyles 126 as well as the exterior surface of first anterior flange 123. First femoral prosthesis 120 also includes first peripheral wall 132 spanning first bone contacting surface 122 and first articulating surface 124. First peripheral wall 132 defines first profile 134.

Second femoral prosthesis 140 is illustrated in dashed lines in FIG. 7 to indicate a second femoral prosthesis having second profile 154 different than first profile 134 of first femoral prosthesis 120. In one embodiment, as illustrated in FIG. 7, second profile 154 of second femoral prosthesis 140 is geometrically analogous to, but smaller than, first profile 134 of first femoral prosthesis 120. Second femoral prosthesis 140, similar to first femoral prosthesis 120, generally includes second bone contacting surface 142 and opposing second articulating surface 144, each extending between second anterior flange 143 and second posterior side 145. Second bone contacting surface 142 is adapted to affix second femoral prosthesis 140 to a distal portion of femur F, such as with bone cement and/or porous bone-ingrowth material. Second femoral prosthesis 140 also includes a pair of second condyles 146, i.e., a medial condyle and a lateral condyle, each including second posterior condyle 147 and second distal condyle 148. Second articulating surface 144 is disposed generally opposite second bone contacting surface 142, and is comprised of the exterior surfaces of second condyles 146 as well as the exterior surface of second anterior flange 143. Second femoral prosthesis 140 also includes second peripheral wall 152 spanning second bone contacting surface 142 and second articulating surface 144. Second peripheral wall 152 defines second profile 154. In the embodiment illustrated in FIG. 7, the only difference between second femoral prosthesis 140 and first femoral prosthesis 120 is that second profile 154 is smaller in a M/L dimension than first profile 134 of first femoral prosthesis 120. For example, the M/L dimension of the anterior facet (e.g., FIG. 3, 44A) of first profile 134 of first femoral prosthesis 120 may be approximately 3.70-4.57 mm larger than the M/L dimension of the anterior facet of second profile 154 of second femoral prosthesis 140. The M/L dimension of the anterior chamfer facet (e.g., FIG. 3, 46A) of first profile 134 of first femoral prosthesis 120 may be approximately 4.19-5.76 mm larger than the M/L dimension of the anterior chamfer facet of second profile 154 of second femoral prosthesis 140. The M/L dimension of the distal facet (e.g., FIG. 3, 48A) of first profile 134 of first femoral prosthesis 120 may be approximately 3.97-5.71 mm larger than the M/L dimension of the distal facet of second profile 154 of second femoral prosthesis 140. The M/L dimension of the posterior chamfer facet (e.g., FIG. 3, 50A) of first profile 134 of first femoral prosthesis 120 may be approximately 4.01-6.00 mm larger than the M/L dimension of the posterior chamfer facet of second profile 154 of second femoral prosthesis 140. The M/L dimension of the posterior facet (e.g., FIG. 3, 52A) of first profile 134 of first femoral prosthesis 120 may be approximately 4.00-6.00 mm larger than the M/L dimension of the posterior facet of second profile 154 of second femoral prosthesis 140. First femoral prosthesis 120 defining first profile 134 could be a standard femoral prosthesis and second femoral prosthesis 140 defining second profile 154 having a smaller M/L dimension than first profile 134 could be a narrow femoral prosthesis in accordance with femoral prostheses described in U.S. Patent Application Publication No. 2007/0260323, published Nov. 8, 2007, entitled "Distal Femoral Knee Prostheses," the entire disclosure of which is hereby expressly incorporated herein by reference.

Second femoral prosthesis 140 and first femoral prosthesis 120 of the present disclosure may be constructed of any biocompatible ceramic or metal, including, but not limited to, titanium, a titanium alloy, cobalt chromium, cobalt chromium molybdenum, porous tantalum, or a combination of these materials, for example. Some or all of the non-articulating portions of first femoral prosthesis 120 and second femoral prosthesis 140 may include a highly porous biomaterial useful as a bone substitute and as cell and tissue receptive material. A highly porous biomaterial may have a porosity as low as 55%, 65%, or 75% or as high as 80%, 85%, or 90%. An example of such a material is produced using Trabecular Metal™ technology generally available from Zimmer, Inc., of Warsaw, Ind. Trabecular Metal™ is a trademark of Zimmer, Inc. Such a material may be formed from a reticulated vitreous carbon foam substrate which is infiltrated and coated with a biocompatible metal, such as tantalum, by a chemical vapor deposition ("CVD") process in the manner disclosed in detail in U.S. Pat. No. 5,282,861 to Kaplan, the entire disclosure of which is expressly incorporated herein by reference. In addition to tantalum, other metals such as niobium, or alloys of tantalum and niobium with one another or with other metals may also be used.

Generally, the porous tantalum structure includes a large plurality of ligaments defining open spaces therebetween, with each ligament generally including a carbon core covered by a thin film of metal such as tantalum, for example. The open spaces between the ligaments form a matrix of continuous channels having no dead ends, such that growth of cancellous bone through the porous tantalum structure is uninhibited. The porous tantalum may include up to 75%, 85%, or more void space therein. Thus, porous tantalum is a lightweight, strong porous structure which is substantially uniform and consistent in composition, and closely resembles the structure of natural cancellous bone, thereby providing a matrix into which cancellous bone may grow to provide fixation of second femoral prosthesis 140 and first femoral prosthesis 120 to the patient's bone.

The porous tantalum structure may be made in a variety of densities in order to selectively tailor the structure for particular applications. In particular, as discussed in the above-incorporated U.S. Pat. No. 5,282,861, the porous tantalum may be fabricated to virtually any desired porosity and pore size, and can thus be matched with the surrounding natural bone in order to provide an improved matrix for bone ingrowth and mineralization.

Referring to FIG. 7, articulating surfaces 124, 144 of first and second femoral prostheses 120, 140 ride on bearing articular surfaces 184 of tibial bearing component 182. Tibial bearing component 182 is positioned on tibial base plate 180 and tibial base plate 180 is positioned on resected proximal tibia surface 179 of proximal tibia T.

Although in the exemplary embodiment of FIG. 7, first femoral prosthesis 120 and second femoral prosthesis 140 are illustrated as bicondylar femoral prostheses, i.e., a femoral prosthesis having a medial condyle and a lateral condyle, it is contemplated that other femoral prostheses may be utilized in accordance with the present disclosure such as a unicondylar femoral prosthesis for a unicondylar knee arthroplasty. A unicondylar femoral prosthesis includes a single condyle having a distal and posterior condyle portion and may replace either a medial or lateral compartment of a distal femur. Referring to FIGS. 1-3, 5, 6 and 8-10, although provisional femoral components 20A, 20B are also illustrated as bicondylar provisional femoral components, i.e., a provisional femoral component having a first condyle and a second condyle, it is contemplated that other provisional femoral components may be utilized in accordance with the present disclosure such as a unicondylar provisional femoral component for a unicondylar knee arthroplasty. For example, first femoral prostheses 120, 140 and provisional femoral components 20A, 20B could be part of a unicondylar knee system in accordance with the unicondylar knee system described in the "Zimmer® Unicompartmental High Flex Knee, Intramedullary, Spacer Block Option and Extramedullary Minimally Invasive Surgical Techniques" brochure, copyright 2004, 2005, 2009, published by Zimmer, Inc., the entire disclosure of which is hereby expressly incorporated by reference herein.

In the exemplary embodiments of FIGS. 1-3, 5, 6 and 8-12, provisional femoral components 20A, 20B, 20C each can be used with first femoral prosthesis 120 and second femoral prosthesis 140 to form a femoral prosthesis system of the present disclosure.

Referring to FIGS. 1-3 and 6, provisional femoral component 20A includes provisional peripheral wall 53A spanning provisional articulating surface 24A and provisional bone contacting surface 22A. Provisional peripheral wall 53A includes a plurality of visual indicators. For example, provisional peripheral wall 53A includes first visual indicators 54A and second visual indicators 58A spaced in an alternating manner along provisional peripheral wall 53A. First visual indicators 54A and second visual indicators 58A provide indicating means for simultaneously visually representing two different femoral prosthesis profiles. First visual indicators 54A of provisional femoral component 20A are formed as protrusions and include exterior peripheral walls 56A spaced along provisional peripheral wall 53A. Second visual indicators 58A of provisional femoral component 20A are formed as cutouts or notches spaced along provisional peripheral wall 53A and disposed between first visual indicators 54A. Each notch includes an indicator wall, i.e., notch interior wall 62A. First visual indicators 54A and second visual indicators 58A are each spaced along provisional peripheral wall 53A and are each part of peripheral wall 53A. A plurality of first visual indicators 54A cooperate to visually represent a relatively larger or standard profile of a femoral prosthesis. For example, first visual indicators 54A cooperate to visually represent first profile 134 of first femoral prosthesis 120 (FIG. 7). A plurality of second visual indicators 58A cooperate to visually represent a profile of a femoral prosthesis smaller in a M/L dimension than first profile 134 of first femoral prosthesis 120 (FIG. 7). For example, second visual indicators 58A cooperate to visually represent second profile 154 of second femoral prosthesis 140 (FIG. 7). In this manner, provisional femoral component 20A is nominally sized to represent a relatively larger profile of a femoral prosthesis, i.e., exterior peripheral walls 56A of first visual indicators 54A cooperate to visually represent a relatively larger profile and notch interior walls 62A of second visual indicators 58A cooperate to visually represent a relatively smaller profile.

In one embodiment, one second visual indicator 58A, e.g., one notch including notch interior wall 62A, can be disposed on each facet, i.e., one notch disposed on each of anterior facet 44A, anterior chamfer facet 46A, distal facet 48A, posterior chamfer facet 50A, and posterior facet 52A. In another embodiment, one second visual indicator 58A can be disposed on respective medial/lateral peripheries on each facet, i.e., anterior facet 44A, anterior chamfer facet 46A, distal facet 48A, posterior chamfer facet 50A, and posterior facet 52A. In another embodiment, as illustrated in FIGS. 1-3, two second visual indicators 58A, i.e., two notches each including notch interior wall 62A, can be disposed on respective medial/lateral peripheries of anterior facet 44A, and one second visual indicator 58A can be disposed on respective medial/lateral peripheries on each of anterior chamfer facet 46A, distal facet 48A, posterior chamfer facet 50A, and posterior facet 52A. In some embodiments, second visual indicators 58A can be centralized on a respective facet. Second visual indicators 58A are disposed along provisional peripheral wall 53A so that the geometry between each notch interior wall 62A can be effectively interpolated. In this manner, second visual indicators 58A cooperate to visually represent a profile of a femoral prosthesis smaller in a M/L dimension than first profile 134 of first femoral prosthesis 120 (FIG. 7).

In another embodiment, referring to FIGS. 8-10, provisional femoral component 20B includes provisional peripheral wall 53B spanning provisional articulating surface 24B and provisional bone contacting surface 22B. Provisional peripheral wall 53B includes a plurality of visual indicators. For example, provisional peripheral wall 53B includes first visual indicators 54B and second visual indicators 66B spaced in an alternating manner along provisional peripheral wall 53B. In this embodiment, first visual indicators 54B are formed as notches and include interior peripheral walls 62B spaced along provisional peripheral wall 53B and disposed between second visual indicators 66B. Second visual indicators 66B are formed as protrusions spaced along provisional peripheral wall 53B and disposed between first visual indicators 54B. Each protrusion includes an indicator wall, i.e., protrusion exterior wall 70B. First visual indicators 54B and second visual indicators 66B are each spaced along provisional peripheral wall 53B and are each part of peripheral wall 53B. A plurality of first visual indicators 54B cooperate to visually represent a relatively smaller or narrow profile of a femoral prosthesis. For example, first visual indicators 54B cooperate to visually represent second profile 154 of second femoral prosthesis 140 (FIG. 7). A plurality of second visual indicators 66B cooperates to visually represent a relatively larger or standard profile of a femoral prosthesis. For example, second visual indicators 66B cooperate to visually represent first profile 134 of first femoral prosthesis 120 (FIG. 7). In this manner, provisional femoral component 20B is nominally sized to represent a relatively smaller profile of a femoral prosthesis, i.e., interior peripheral walls 62B of first visual indicators 54B cooperate to visually represent a relatively smaller profile and protrusion exterior walls 70B of second visual indicators 66B cooperate to visually represent a relatively larger profile. In both exemplary embodiments illustrated in FIGS. 1-3, 6, and 8-10, the visual indicators include a respective alternating arrangement of protrusions and notches.

In one embodiment, one second visual indicator 66B, e.g., one protrusion including protrusion exterior wall 70B, can be disposed on each facet, i.e., one protrusion disposed on each of anterior facet 44B, anterior chamfer facet 46B, distal facet 48B, posterior chamfer facet 50B, and posterior facet 52B. In another embodiment, one second visual indicator 66B can be disposed on respective medial/lateral peripheries on each facet, i.e., anterior facet 44B, anterior chamfer facet 46B, distal facet 48B, posterior chamfer facet 50B, and posterior facet 52B. In another embodiment, as illustrated in FIGS. 8 and 9, four second visual indicators 66B, i.e., four protrusions each including protrusion exterior wall 70B, can be disposed along provisional peripheral wall 53B of anterior facet 44B. In some embodiments, second visual indicators 66B can be centralized on a respective facet. Second visual indicators 66B are disposed along provisional peripheral wall 53B so that the geometry between each protrusion exterior wall 70B can be effectively interpolated. In this manner, second visual indicators 66B cooperate to visually represent a profile of a femoral prosthesis larger in a M/L dimension than second profile 154 of second femoral prosthesis 140 (FIG. 7).

Referring to FIGS. 8, 9, 11 and 12, while provisional femoral components 20B, 20C are shown with regard to a left provisional femoral component for a left knee configuration, it will be appreciated that the present disclosure is equally applicable to a right provisional femoral component for a right knee configuration.

Referring to FIGS. 1-12, the use of a femoral prosthesis system of the present disclosure to determine a size of a femoral prosthesis for a prosthetic knee joint including proximal tibia T (FIG. 7) and distal femur F (FIG. 7) will now be described. Referring to FIGS. 1, 7, 8 and 11, a user such as a surgeon obtains a femoral prosthesis system in accordance with the present disclosure, i.e., one of provisional femoral components 20A, 20B, 20C, first femoral prosthesis 120, and second femoral prosthesis 140. Next, referring to FIG. 5, the surgeon can position provisional bone contacting surface 22A of provisional femoral component 20A, for example, on resected distal femur surface 160. With provisional femoral component 20A, or provisional femoral component 20B, 20C, positioned on distal femur F, the surgeon can use first visual indicators 54A to visually represent first profile 134 of first femoral prosthesis 120 (FIG. 7) and second visual indicators 58A to simultaneously visually represent second profile 154 of second femoral prosthesis 140 (FIG. 7). The surgeon can simultaneously use first visual indicators 54A and second visual indicators 58A to visually confirm which are most properly aligned with perimeter 162 (FIG. 5) of resected distal femur surface 160 (FIG. 5), i.e., the perimeter of each of anterior cut 164, anterior chamfer cut 166, distal cut 168, posterior chamfer cut 170, and posterior cut 172. In one embodiment, the surgeon can use first visual indicators 54A and second visual indicators 58A to visually lateralize provisional femoral component 20A with distal femur F. For example, referring to FIG. 5, if distal femur F is a left knee, the surgeon can reference anterior left lateral portion 85A of provisional femoral component 20A with anterior lateral edge 173 of distal femur F. In this manner, the surgeon can determine if a standard femoral prosthesis or a narrow femoral prosthesis should be implanted in the knee joint based on which of first visual indicators 54A and second visual indicators 58A in anterior left lateral portion 85A of provisional femoral component 20A are more aligned with anterior lateral edge 173 of distal femur F. The surgeon can then select one of first femoral prosthesis 120 and second femoral prosthesis 140 for implantation in the knee joint based on first visual indicators 54A and second visual indicators 58A of provisional femoral component 20A.

Referring to FIG. 5, in another embodiment, because provisional femoral component 20A can be an ambidextrous provisional femoral component, as will be discussed in more detail below, if distal femur F is a right knee, the surgeon can reference anterior right lateral portion 86A of provisional femoral component 20A with anterior lateral edge 175 of distal femur F to visually lateralize provisional femoral component 20A with a right distal femur F.

In another embodiment, the present disclosure provides a provisional femoral component including a patellofemoral flange having two sulci and a central ridge between the two sulci. Accordingly, the provisional femoral component of the present disclosure is capable of being positioned on a resected distal femur surface of both a right and left knee. Although in the exemplary embodiment of FIGS. 1-6, provisional femoral component 20A is illustrated as a bicondylar provisional femoral component, i.e., a provisional femoral component having a first condyle and a second condyle, it is contemplated that other provisional femoral components may be utilized in accordance with the present disclosure such as a patellofemoral flange femoral component for a patellofemoral joint system. For example, provisional femoral component 20A could be part of a patellofemoral joint system in accordance with the patellofemoral joint system described in the "Zimmer® Gender Solutions™ Patello-Femoral Joint (PFJ) System, Surgical Technique" brochure, copyright 2008, 2009, published by Zimmer, Inc., the entire disclosure of which is hereby expressly incorporated by reference herein.

Referring to FIGS. 2 and 4, patellofemoral flange 34A of provisional femoral component 20A generally includes non-articulating surface or bone contacting surface 72A and opposing articulating surface 74A. Referring to FIG. 4, in one embodiment, bone contacting surface 72A is planar. Bone contacting surface 72A is adapted to affix patellofemoral flange 34A to a distal portion of a femur such as distal femur F shown in FIG. 5. Articulating surface 74A of patellofemoral flange 34A includes first sulcus 76A formed in patellofemoral flange 34A, second sulcus 78A formed in patellofemoral flange 34A, and raised mid-line or central ridge 80A disposed between first sulcus 76A and second sulcus 78A. Patellofemoral flange 34A also includes first anterior flange 82A and second anterior flange 84A extending along respective medial/lateral peripheries of patellofemoral flange 34A. Referring to FIG. 4, first anterior flange 82A and second anterior flange 84A each have an anterior flange thickness, and central ridge 80A has a central ridge thickness. In one embodiment, the anterior flange thickness of first anterior flange 82A and second anterior flange 84A is greater than the central ridge thickness of central ridge 80A. First sulcus 76A and second sulcus 78A are each disposed between first anterior flange 82A and second anterior flange 84A. In one embodiment, patellofemoral flange 34A has a sagittal plane of symmetry and central ridge 80A of patellofemoral flange 34A is disposed along the sagittal plane of symmetry.

For purposes of this disclosure, patellofemoral flange 34A is defined as a flange sized to fit on a distal femur and which articulates with the patella of a knee joint during normal articulation of the knee joint through a normal range of motion. For example, articulating surface 74A of patellofemoral flange 34A is sized and shaped for articulating with a natural or prosthetic patella during normal articulation of a knee joint through a normal range of motion. First sulcus 76A and second sulcus 78A are each defined as a sulcus or patellofemoral groove of patellofemoral flange 34A sized and shaped to provide a groove to receive a natural or prosthetic patella of a knee joint during normal articulation of the knee joint through a normal range of motion.

In one embodiment, as illustrated in FIG. 4, patellofemoral flange 34A is formed by conceptually merging right lateral portion 86A of a right femoral component and left lateral portion 85A of a left femoral component to form first sulcus 76A, second sulcus 78A, and central ridge 80A disposed between first sulcus 76A and second sulcus 78A. Referring to FIG. 4, dashed lines illustrate medial portion 87A of a left femoral component and medial portion 88A of a right femoral component 88A. First sulcus 76A is formed in patellofemoral flange 34A between central ridge 80A and first anterior flange 82A and second sulcus 78A is formed in patellofemoral flange 34A between second anterior flange 84A and central ridge 80A.

Referring to FIGS. 2 and 4, the use of patellofemoral flange 34A during trialing of the knee joint to determine a proper size of a patellofemoral flange prosthesis will now be described. Once patellofemoral flange 34A is properly positioned adjacent anterior cut 164 (FIG. 5) of resected distal femur surface 160 (FIG. 5), a surgeon can perform range of motion testing of the knee joint and track articulation of the patella with patellofemoral flange 34A. Central ridge 80 provides tactile feedback to the surgeon to indicate when the patella is dislocating medially. In this manner, when using patellofemoral flange 34A with a left distal femur of a left knee joint, first anterior flange 82A of left lateral portion 85A simulates a lateral aspect of patellofemoral flange 34A and central ridge 80A simulates a medial aspect of patellofemoral flange 34A. In this manner, the surgeon can track the patella through range of motion testing and receive feedback when the patella is dislocating medially, i.e., when the patella rides over central ridge 80A and out of first sulcus 76A. In this embodiment, second anterior flange 84A simulates a medial aspect of patellofemoral flange 34A.

Patellofemoral flange 34A can also be used on a right distal femur of a right knee joint. For example, with patellofemoral flange 34A positioned adjacent a right distal femur of a right knee joint, second anterior flange 84A of right lateral portion 86A simulates a lateral aspect of patellofemoral flange 34A and central ridge 80A simulates a medial aspect of patellofemoral flange 34A. In this manner, the surgeon can track the patella through range of motion testing and receive feedback when the patella is dislocating medially, i.e., when the patella rides over central ridge 80A and out of second sulcus 78A. In this embodiment, first anterior flange 82A simulates a medial aspect of patellofemoral flange 34A.

Patellofemoral flange 34A of the present disclosure may be used with a patellofemoral system designed to provide a partial knee replacement in which only the patellofemoral compartment of the distal femur receives a prosthesis. In another embodiment, patellofemoral flange 34A of the present disclosure can be used with provisional femoral component 20A as illustrated in FIGS. 1-6 for use in a total knee arthroplasty procedure. In such an embodiment, a provisional femoral component is provided which can be positioned on the distal femur of both a right and left knee joint, and which includes first visual indicators 54A spaced along provisional peripheral wall 53A to visually represent a first profile of a first femoral prosthesis and second visual indicators 58A spaced along provisional peripheral wall 53A to visually represent a second profile of a second femoral prosthesis as discussed in more detail above.

Referring to FIGS. 8-12, provisional femoral components 20B, 20C each include patellofemoral flange 34B, 34C having one sulcus 36B, 36C. In alternative embodiments, provisional femoral components 20B, 20C can each include patellofemoral flanges 34B, 34C having two sulci as described above with respect to patellofemoral flange 34A of the embodiments of FIGS. 1-6. In such embodiments, provisional femoral components 20B, 20C could each be used on both a right and left distal femur of both a right and left knee joint.

Figure 6:
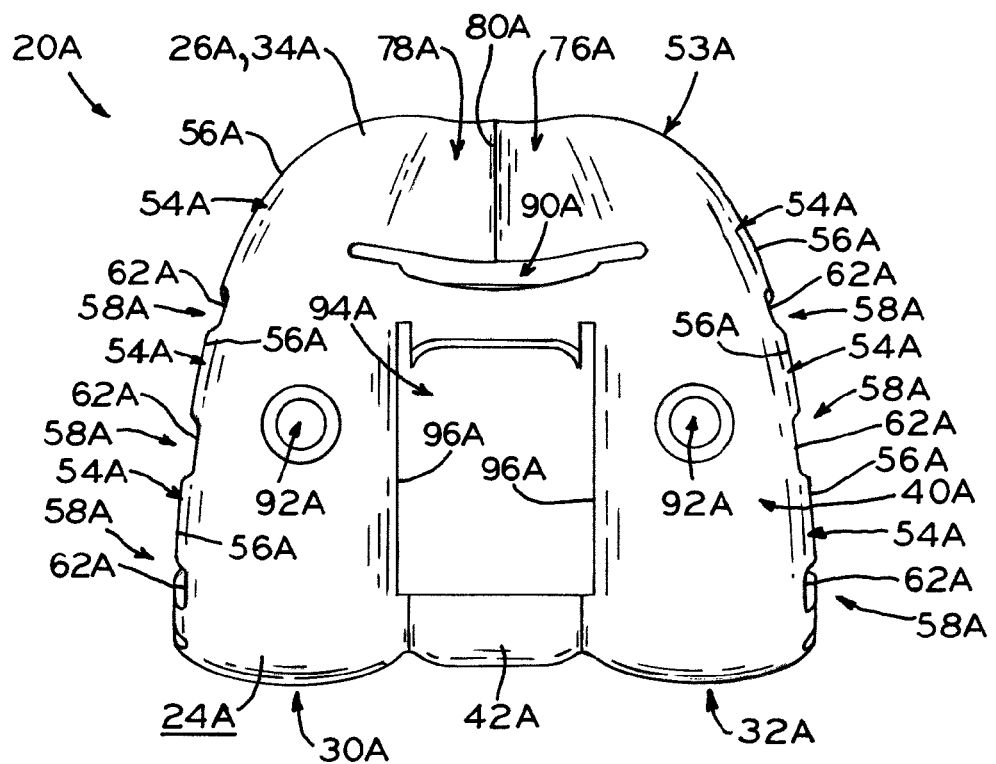
FIG. 6 is a bottom elevation view of the provisional femoral component of FIG. 1.

Referring to FIGS. 6, 8, and 11, provisional femoral components 20A, 20B, 20C of the present disclosure can also be used as a femoral cut guide for preparing a distal femur to receive a prosthetic femoral component of a knee implant, the prosthetic femoral component comprising a posterior stabilized prosthesis including a central box. Particularly, provisional femoral component 20A, 20B, 20C may be used to remove bone from distal femur F (FIGS. 5 and 7) to accommodate a box projection of a posterior stabilized prosthetic femoral component. In one embodiment, the box projection can include medial and lateral sidewalls. In some embodiments, the box projection can also include an anterior sidewall.

Referring to FIGS. 6 and 9, provisional femoral components 20A, 20B respectively include guide slot 90A, 90B and opening 94A, 94B having a pair of side walls 96A, 96B. Referring to FIGS. 6 and 11, provisional femoral components 20A, 20C each include apertures 92A that are sized to be used for preparing holes for the femoral lugs or pegs of the femoral implant. Apertures 92A can also be sized to receive bone screws and/or pins for anchoring provisional femoral components 20A, 20C to a patient's distal femur F (FIGS. 5 and 7). In one embodiment, provisional femoral component 20B may also include apertures similar to apertures 92A, 92C. With provisional femoral components 20A, 20B positioned on a resected distal femur surface, the knee joint can be articulated through a full range of motion testing. Provisional femoral components 20A, 20B, 20C of the present disclosure may be used as a femoral cut guide in accordance with the femoral cut guide described in U.S. patent application Ser. No. 12/844,495, filed Jul. 27, 2010, entitled "Femoral Cut Guide," the entire disclosure of which is hereby expressly incorporated herein by reference.

In one embodiment, referring to FIGS. 11 and 12, provisional femoral component 20C may include receiving slot 98C and keyway or track 100 formed in each side wall 96C. In such an embodiment, modular insert component 102C may be removably attached to provisional femoral component 20C in opening 94C between side walls 96C. When assembled, a surgeon may verify proper articulation of provisional femoral component 20C against a patient's adjacent patella and tibia. Modular insert component 102C includes lower patellofemoral track 104C, locking tabs 106C, key or insertion rails 108C, and modular insert component cutouts 110C. To secure modular insert component 102C to provisional femoral component 20C, locking tabs 106C and insertion rails 108C are respectively positioned within receiving slots 98C and tracks 100C of provisional femoral component 20C. In one embodiment, modular insert component 102C provides the most distal aspect, i.e., lower patellofemoral track 104C, of the patella track of provisional femoral component 20C. In such an embodiment, with modular insert component 102C secured to provisional femoral component 20C and provisional femoral component 20C positioned on a resected distal femur surface, the knee joint can be articulated through a full range of motion testing. Without modular insert component 102 secured to provisional femoral component 20C, the knee joint can still be articulated through partial range of motion testing. Modular insert component cutouts 110C allow a femoral inserter/extractor surgical instrument to engage modular insert component 102C for easy insertion and removal of modular insert component 102C. In one embodiment, locking tabs 106C can be removed from the anterior portion of modular insert component 102C. In such an embodiment, locking tabs 106C can be a part of insertion rails 108C and function to secure modular insert component 102C to provisional femoral component 20C.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A femoral prosthesis system, comprising:
    a first femoral prosthesis, comprising:
        a first condyle, said first condyle defining a first articulating surface and an opposing first bone contacting surface; and
        a first peripheral wall spanning said first articulating surface and said first bone contacting surface, said first peripheral wall defining a first profile;
    a second femoral prosthesis, comprising:
        a second condyle, said second condyle defining a second articulating surface and an opposing second bone contacting surface; and
        a second peripheral wall spanning said second articulating surface and said second bone contacting surface, said second peripheral wall defining a second profile, wherein said second profile is different than said first profile;
    a provisional femoral component, comprising:
        a provisional condyle, said provisional condyle defining a provisional articulating surface and an opposing provisional bone contacting surface;
        a provisional peripheral wall spanning said provisional articulating surface and said provisional bone contacting surface; and
        at least one first visual indicator and at least one second visual indicator spaced along said provisional peripheral wall, said at least one first visual indicator visually representing said first profile of said first femoral prosthesis, and said at least one second visual indicator visually representing said second profile of said second femoral prosthesis.

2. The femoral prosthesis system of claim 1, wherein said provisional femoral component further comprises:
    a plurality of first visual indicators spaced along said provisional peripheral wall, said plurality of first visual indicators cooperating to visually represent said first profile of said first femoral prosthesis; and
    a plurality of second visual indicators spaced along said provisional peripheral wall, said plurality of second visual indicators cooperating to visually represent said second profile of said second femoral prosthesis.

3. The femoral prosthesis system of claim 2, wherein said plurality of first and second visual indicators comprise a respective alternating arrangement of protrusions and notches.

4. The femoral prosthesis system of claim 2, wherein:
    said first condyle of said first femoral prosthesis comprises a first distal condyle portion and a first posterior condyle portion;
    said second condyle of said second femoral prosthesis comprises a second distal condyle portion and a second posterior condyle portion; and
    said provisional condyle of said provisional femoral component comprises a provisional distal condyle portion and a provisional posterior condyle portion.

5. The femoral prosthesis system of claim 2, wherein:
    said first condyle comprises a medial and lateral pair of first condyles;
    said second condyle comprises a medial and lateral pair of second condyles; and
    said provisional condyle comprises a medial and lateral pair of provisional condyles.

\* \* \* \* \*

UNITED STATES PATENT AND TRADEMARK OFFICE
CERTIFICATE OF CORRECTION

PATENT NO. : 8,551,179 B2  Page 1 of 1
APPLICATION NO. : 13/161624
DATED : October 8, 2013
INVENTOR(S) : Jones et al.

It is certified that error appears in the above-identified patent and that said Letters Patent is hereby corrected as shown below:

On the Title page, in column 2, Item (56) under "Other Publications", line 1-3, delete "Partial Search Report mailed Jul. 3, 2012 in International Application No. PCT/US2012/038531 from the International Searching Authority." and insert --"International Application Serial No. PCT/US2012/038531, Partial Search Report mailed Jul. 3, 2012".--, therefor On Title page 2, in column 2, Item (56) under "Other Publications", line 2, after "Inc.", insert --,--, therefor On Title page 2, in column 2, Item (56) under "Other Publications", line 5, after "Inc.", insert --,--, therefor Signed and Sealed this
Twenty-fifth Day of November, 2014

Michelle K. Lee
*Deputy Director of the United States Patent and Trademark Office*